United States Patent
An et al.

(10) Patent No.: US 12,037,390 B2
(45) Date of Patent: Jul. 16, 2024

(54) LEPTIN ANTIBODIES AND METHOD OF REDUCING LEPTIN

(71) Applicant: Board of Regents, The University of Texas System, Austin, TX (US)

(72) Inventors: Zhiqiang An, Dallas, TX (US); Ningyan Zhang, Dallas, TX (US); Philipp E. Scherer, Dallas, TX (US); Shangang Zhao, Dallas, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 18/365,969

(22) Filed: Aug. 4, 2023

(65) Prior Publication Data
US 2023/0374126 A1 Nov. 23, 2023

Related U.S. Application Data

(60) Division of application No. 17/124,481, filed on Dec. 16, 2020, now Pat. No. 11,760,799, which is a continuation of application No. PCT/US2019/037236, filed on Jun. 14, 2019.

(60) Provisional application No. 62/685,997, filed on Jun. 16, 2018.

(51) Int. Cl.
*C07K 16/18* (2006.01)
*A61P 3/04* (2006.01)
*C07K 16/26* (2006.01)
*A61K 39/00* (2006.01)

(52) U.S. Cl.
CPC ............ *C07K 16/26* (2013.01); *A61P 3/04* (2018.01); *A61K 2039/505* (2013.01); *C07K 2317/24* (2013.01); *C07K 2317/76* (2013.01); *C07K 2317/92* (2013.01)

(58) Field of Classification Search
None
See application file for complete search history.

(56) References Cited

PUBLICATIONS

Mahmoudian et al. Hybridoma 31(5): 372-377, 2012.*
Obradovic et al. Front. In Endocrinol. 12: 1-14, 2021.*
Izquierdo et al. Nutrients 11: 1-11, 2019.*
Korner et al. N. Engl. J. Med. 349(10): 926-928, 2003.*
Science 280: 1363-1387, 1998.*
Kanasaki et al. J. Biomed. Biotech. vol. 2011, Article ID 197636, 11 pages, 2011: 197636. doi:10.1155/2011/197636.*
Martinez (Proc. Nutr. Soc. 59: 337-345, 2000).*

* cited by examiner

*Primary Examiner* — Christine J Saoud
(74) *Attorney, Agent, or Firm* — Parker Highlander PLLC

(57) ABSTRACT

Antibody antigen binding domains which specifically binds human leptin comprises $V_H$ or $V_L$ CDR1, CDR2 and CDR3 sequences of an hLept antibody. The antibody antigen binding domains and antibodies thereof are useful to treat obesity and diabetes.

4 Claims, 1 Drawing Sheet
Specification includes a Sequence Listing.

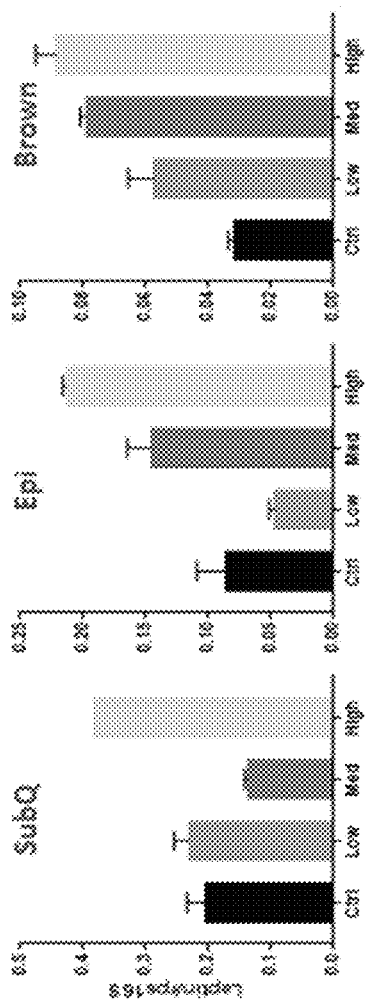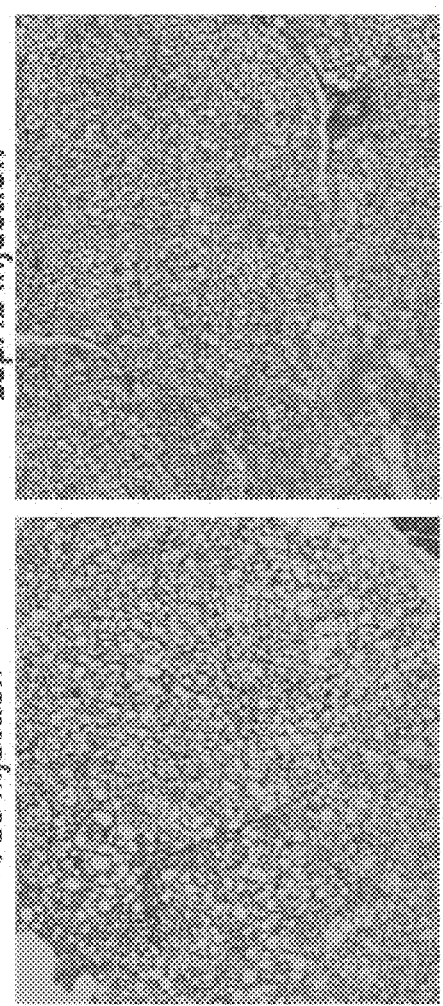
Fig. 1A, Fig. 1B, Fig. 1C, Fig. 1D, Fig. 1E

```
                          SEQUENCE LISTING

Sequence total quantity: 70
SEQ ID NO: 1           moltype = AA   length = 10
FEATURE                Location/Qualifiers
source                 1..10
                       mol_type = protein
                       organism = Homo sapiens
SEQUENCE: 1
GGSVSRGSHY                                                                 10

SEQ ID NO: 2           moltype = AA   length = 7
FEATURE                Location/Qualifiers
source                 1..7
                       mol_type = protein
                       organism = Homo sapiens
SEQUENCE: 2
IHTDGST                                                                     7

SEQ ID NO: 3           moltype = AA   length = 10
FEATURE                Location/Qualifiers
source                 1..10
                       mol_type = protein
                       organism = Homo sapiens
SEQUENCE: 3
AREPGGALNF                                                                 10

SEQ ID NO: 4           moltype = AA   length = 8
FEATURE                Location/Qualifiers
source                 1..8
                       mol_type = protein
                       organism = Homo sapiens
SEQUENCE: 4
GYTFTGYY                                                                    8

SEQ ID NO: 5           moltype = AA   length = 8
FEATURE                Location/Qualifiers
source                 1..8
                       mol_type = protein
                       organism = Homo sapiens
SEQUENCE: 5
INPNSGGT                                                                    8

SEQ ID NO: 6           moltype = AA   length = 19
FEATURE                Location/Qualifiers
source                 1..19
                       mol_type = protein
                       organism = Homo sapiens
SEQUENCE: 6
ASGKTYYDFW SGGRRGMDV                                                       19

SEQ ID NO: 7           moltype = AA   length = 8
FEATURE                Location/Qualifiers
source                 1..8
                       mol_type = protein
                       organism = Homo sapiens
SEQUENCE: 7
GGTFSSYA                                                                    8
```

```
SEQ ID NO: 8              moltype = AA  length = 8
FEATURE                   Location/Qualifiers
source                    1..8
                          mol_type = protein
                          organism = Homo sapiens
SEQUENCE: 8
IIPIFGTA                                                                     8

SEQ ID NO: 9              moltype = AA  length = 15
FEATURE                   Location/Qualifiers
source                    1..15
                          mol_type = protein
                          organism = Homo sapiens
SEQUENCE: 9
ARSQVPSSYY YGMDV                                                            15

SEQ ID NO: 10             moltype = AA  length = 8
FEATURE                   Location/Qualifiers
source                    1..8
                          mol_type = protein
                          organism = Homo sapiens
SEQUENCE: 10
GFTFSSYA                                                                     8

SEQ ID NO: 11             moltype = AA  length = 8
FEATURE                   Location/Qualifiers
source                    1..8
                          mol_type = protein
                          organism = Homo sapiens
SEQUENCE: 11
ISYDGSNK                                                                     8

SEQ ID NO: 12             moltype = AA  length = 12
FEATURE                   Location/Qualifiers
source                    1..12
                          mol_type = protein
                          organism = Homo sapiens
SEQUENCE: 12
ARGREYYYYM DV                                                               12

SEQ ID NO: 13             moltype = AA  length = 8
FEATURE                   Location/Qualifiers
source                    1..8
                          mol_type = protein
                          organism = Homo sapiens
SEQUENCE: 13
GYTFTSYY                                                                     8

SEQ ID NO: 14             moltype = AA  length = 8
FEATURE                   Location/Qualifiers
source                    1..8
                          mol_type = protein
                          organism = Homo sapiens
SEQUENCE: 14
INPSGGST                                                                     8

SEQ ID NO: 15             moltype = AA  length = 13
FEATURE                   Location/Qualifiers
source                    1..13
                          mol_type = protein
                          organism = Homo sapiens
SEQUENCE: 15
ARGFGYGGKA LDY                                                              13

SEQ ID NO: 16             moltype = AA  length = 8
FEATURE                   Location/Qualifiers
source                    1..8
                          mol_type = protein
                          organism = Homo sapiens
SEQUENCE: 16
SSNIGSNT                                                                     8

SEQ ID NO: 17             moltype = AA  length = 11
FEATURE                   Location/Qualifiers
source                    1..11
                          mol_type = protein
                          organism = Homo sapiens
SEQUENCE: 17
```

ASWDDSLNGV V                                                                              11

SEQ ID NO: 18          moltype = AA  length = 6
FEATURE                Location/Qualifiers
source                 1..6
                       mol_type = protein
                       organism = Homo sapiens SEQUENCE: 18
QSVSRY                                                                                    6

SEQ ID NO: 19          moltype = AA  length = 9
FEATURE                Location/Qualifiers
source                 1..9
                       mol_type = protein
                       organism = Homo sapiens SEQUENCE: 19
QQTYSTPWT                                                                                 9

SEQ ID NO: 20          moltype = AA  length = 9
FEATURE                Location/Qualifiers
source                 1..9
                       mol_type = protein
                       organism = Homo sapiens SEQUENCE: 20
NSNIGAGYH                                                                                 9

SEQ ID NO: 21          moltype = AA  length = 11
FEATURE                Location/Qualifiers
source                 1..11
                       mol_type = protein
                       organism = Homo sapiens SEQUENCE: 21
QSYDRSRGGW F                                                                              11

SEQ ID NO: 22          moltype = AA  length = 6
FEATURE                Location/Qualifiers
source                 1..6
                       mol_type = protein
                       organism = Homo sapiens SEQUENCE: 22
NIARKS                                                                                    6

SEQ ID NO: 23          moltype = AA  length = 9
FEATURE                Location/Qualifiers
source                 1..9
                       mol_type = protein
                       organism = Homo sapiens SEQUENCE: 23
QVWDNSDYV                                                                                 9

SEQ ID NO: 24          moltype = AA  length = 6
FEATURE                Location/Qualifiers
source                 1..6
                       mol_type = protein
                       organism = Homo sapiens SEQUENCE: 24
QNINSR                                                                                    6

SEQ ID NO: 25          moltype = AA  length = 9
FEATURE                Location/Qualifiers
source                 1..9
                       mol_type = protein
                       organism = Homo sapiens SEQUENCE: 25
QQFDKYSIT                                                                                 9

SEQ ID NO: 26          moltype = DNA  length = 30
FEATURE                Location/Qualifiers
source                 1..30
                       mol_type = other DNA
                       organism = Homo sapiens SEQUENCE: 26
ggtggctccg tcagcagagg tagtcactac                                                          30

SEQ ID NO: 27          moltype = DNA  length = 21
FEATURE                Location/Qualifiers
source                 1..21
                       mol_type = other DNA
                       organism = Homo sapiens

```
SEQUENCE: 27
atccacaccg atgggagcac c                                              21

SEQ ID NO: 28           moltype = DNA   length = 30
FEATURE                 Location/Qualifiers
source                  1..30
                        mol_type = other DNA
                        organism = Homo sapiens
SEQUENCE: 28
gcgagagagc ccgggggcgc cctgaatttc                                     30

SEQ ID NO: 29           moltype = DNA   length = 24
FEATURE                 Location/Qualifiers
source                  1..24
                        mol_type = other DNA
                        organism = Homo sapiens
SEQUENCE: 29
ggatacacct tcaccggcta ctat                                           24

SEQ ID NO: 30           moltype = DNA   length = 24
FEATURE                 Location/Qualifiers
source                  1..24
                        mol_type = other DNA
                        organism = Homo sapiens
SEQUENCE: 30
atcaacccta acagtggtgg caca                                           24

SEQ ID NO: 31           moltype = DNA   length = 57
FEATURE                 Location/Qualifiers
source                  1..57
                        mol_type = other DNA
                        organism = Homo sapiens
SEQUENCE: 31
gcgagtggga aaacgtatta cgatttttgg agtggtggga gacgcggtat ggacgtc       57

SEQ ID NO: 32           moltype = DNA   length = 24
FEATURE                 Location/Qualifiers
source                  1..24
                        mol_type = other DNA
                        organism = Homo sapiens
SEQUENCE: 32
ggaggcacct tcagcagcta tgct                                           24

SEQ ID NO: 33           moltype = DNA   length = 24
FEATURE                 Location/Qualifiers
source                  1..24
                        mol_type = other DNA
                        organism = Homo sapiens
SEQUENCE: 33
atcatcccta tctttggtac agca                                           24

SEQ ID NO: 34           moltype = DNA   length = 45
FEATURE                 Location/Qualifiers
source                  1..45
                        mol_type = other DNA
                        organism = Homo sapiens
SEQUENCE: 34
gcgagaagcc aggtaccatc ctcctactac tacggtatgg acgtc                    45

SEQ ID NO: 35           moltype = DNA   length = 24
FEATURE                 Location/Qualifiers
source                  1..24
                        mol_type = other DNA
                        organism = Homo sapiens
SEQUENCE: 35
ggattcacct tcagtagcta tgct                                           24

SEQ ID NO: 36           moltype = DNA   length = 24
FEATURE                 Location/Qualifiers
source                  1..24
                        mol_type = other DNA
                        organism = Homo sapiens
SEQUENCE: 36
atatcatatg atggaagcaa taaa                                           24

SEQ ID NO: 37           moltype = DNA   length = 36
FEATURE                 Location/Qualifiers
source                  1..36
                        mol_type = other DNA
```

-continued

```
                        organism = Homo sapiens
SEQUENCE: 37
gcgagaggtc gtgaatacta ctactacatg gacgtc                                      36

SEQ ID NO: 38           moltype = DNA  length = 24
FEATURE                 Location/Qualifiers
source                  1..24
                        mol_type = other DNA
                        organism = Homo sapiens
SEQUENCE: 38
ggatacacct tcaccagcta ctat                                                   24

SEQ ID NO: 39           moltype = DNA  length = 24
FEATURE                 Location/Qualifiers
source                  1..24
                        mol_type = other DNA
                        organism = Homo sapiens
SEQUENCE: 39
atcaaccctg gtggtggtag caca                                                   24

SEQ ID NO: 40           moltype = DNA  length = 39
FEATURE                 Location/Qualifiers
source                  1..39
                        mol_type = other DNA
                        organism = Homo sapiens
SEQUENCE: 40
gcgagaggat tcggctacgg tggtaaggcc cttgactac                                   39

SEQ ID NO: 41           moltype = DNA  length = 24
FEATURE                 Location/Qualifiers
source                  1..24
                        mol_type = other DNA
                        organism = Homo sapiens
SEQUENCE: 41
agctccaaca tcggaagtaa tact                                                   24

SEQ ID NO: 42           moltype = DNA  length = 33
FEATURE                 Location/Qualifiers
source                  1..33
                        mol_type = other DNA
                        organism = Homo sapiens
SEQUENCE: 42
gcatcatggg atgacagcct gaatggtgtg gta                                         33

SEQ ID NO: 43           moltype = DNA  length = 18
FEATURE                 Location/Qualifiers
source                  1..18
                        mol_type = other DNA
                        organism = Homo sapiens
SEQUENCE: 43
cagagcgtta gcaggtat                                                          18

SEQ ID NO: 44           moltype = DNA  length = 27
FEATURE                 Location/Qualifiers
source                  1..27
                        mol_type = other DNA
                        organism = Homo sapiens
SEQUENCE: 44
caacagactt acagtacccc gtggacg                                                27

SEQ ID NO: 45           moltype = DNA  length = 27
FEATURE                 Location/Qualifiers
source                  1..27
                        mol_type = other DNA
                        organism = Homo sapiens
SEQUENCE: 45
aactccaaca tcggggcagg ttatcat                                                27

SEQ ID NO: 46           moltype = DNA  length = 33
FEATURE                 Location/Qualifiers
source                  1..33
                        mol_type = other DNA
                        organism = Homo sapiens
SEQUENCE: 46
cagtcctatg acagaagccg gggtggttgg ttt                                         33

SEQ ID NO: 47           moltype = DNA  length = 18
FEATURE                 Location/Qualifiers
source                  1..18
```

```
                                mol_type = other DNA
                                organism = Homo sapiens
SEQUENCE: 47
aacattgcaa gaaaaagt                                                  18

SEQ ID NO: 48              moltype = DNA  length = 27
FEATURE                    Location/Qualifiers
source                     1..27
                                mol_type = other DNA
                                organism = Homo sapiens
SEQUENCE: 48
caggtgtggg ataatagtga ttatgtc                                        27

SEQ ID NO: 49              moltype = DNA  length = 18
FEATURE                    Location/Qualifiers
source                     1..18
                                mol_type = other DNA
                                organism = Homo sapiens
SEQUENCE: 49
cagaatatta atagtagg                                                  18

SEQ ID NO: 50              moltype = DNA  length = 27
FEATURE                    Location/Qualifiers
source                     1..27
                                mol_type = other DNA
                                organism = Homo sapiens
SEQUENCE: 50
caacagtttg ataaatattc gatcact                                        27

SEQ ID NO: 51              moltype = DNA  length = 354
FEATURE                    Location/Qualifiers
source                     1..354
                                mol_type = other DNA
                                organism = Homo sapiens
SEQUENCE: 51
caggtacagc tgcagcagtt gggcccagga ctggtgaagc cttcggagac cctgtccctc    60
acctgcaatg tctctggtgg ctccgtcagc agaggtagtc actactggac ctggatccgg   120
cagcccccag gaaagggact ggagtggatt gggtatatcc acaccgatgg gagcaccaac   180
ttcaatccct ccctcaagag tcgagtcacc atgtcactag acaggtccag gaaccagttc   240
tccctgacgc tgagctctgt gaccgctacg gacacggccg tttattattg tgcgagagag   300
cccgggggcg ccctgaattt ctggggccag ggaaccctgg tcaccgtctc ctca         354

SEQ ID NO: 52              moltype = DNA  length = 330
FEATURE                    Location/Qualifiers
source                     1..330
                                mol_type = other DNA
                                organism = Homo sapiens
SEQUENCE: 52
aattttatgc tgactcagcc accctcaacg tctgggaccc ccgggcagag ggtcaccatc    60
tcttgttctg gaagcagctc caacatcgga agtaatactg taaactggta ccagcagctc   120
ccaggaacgg ccccccaaact cctcatctat agtaataatc agcggccctc aggggtccct   180
gaccgattct ctggctccaa gtctggcacc tcagcctccc tggccatcag tgggctccag   240
tctgaggatg aggctgatta ttattgtgca tcatgggatg acagcctgaa tggtgtggta   300
ttcggcggag ggaccacggt gaccgtcctg                                    330

SEQ ID NO: 53              moltype = DNA  length = 378
FEATURE                    Location/Qualifiers
source                     1..378
                                mol_type = other DNA
                                organism = Homo sapiens
SEQUENCE: 53
caggtgcagc tggtgcagtc tggggctgag gtgaagaagc ctggggcctc agtgaaggtc    60
tcctgcaagg cttctggata caccttcacc ggctactata tgcactgggt gcgacaggcc   120
cctggacaag ggcttgagtg gatgggacgg atcaaccta caggtggtg cacaaactat   180
gcacagaagt ttcagggcag ggtcaccatg accagggaca cgtccatcag cacagcctac   240
atggagctga gcaggctgag atctgacgac acggccgtgt attactgtgc gagtgggaaa   300
acgtattacg attttggag tggtgggaga cgcggtatgg acgtctgggg ccaagggaca   360
atggtcaccg tctcttca                                                 378

SEQ ID NO: 54              moltype = DNA  length = 321
FEATURE                    Location/Qualifiers
source                     1..321
                                mol_type = other DNA
                                organism = Homo sapiens
SEQUENCE: 54
gacatccagt tgacccagtc tccatcctcc ctgtctgcat ctgtaggaga cagagtcacc    60
atcacttgcc gggcaggtca gagcgttagc aggtatttaa attggtttca gcagaaacca   120
gggaaagccc ctaagctcct catctatact tcatccaatt tgcaaagtgg ggtcccatca   180
aggttcagtg ccagtggatc tgggacagat ttcactctca ccatcagcag tctgcaacct   240
```

```
gaggattttg ctacctacta ctgtcaacag acttacagta ccccgtggac gttcggccaa    300
gggaccaagc tggagatcaa a                                              321
```

| SEQ ID NO: 55 | moltype = DNA  length = 366 |
|---|---|
| FEATURE | Location/Qualifiers |
| source | 1..366 |
| | mol_type = other DNA |
| | organism = Homo sapiens |

SEQUENCE: 55
```
caggtgcagc tggtgcagtc tggggctgag gtgaagaagc ctgggtcctc ggtgaaggtc     60
tcctgcaagg cttctggagg caccttcagc agctatgcta tcagctgggt gcgacaggcc    120
cctggacaag ggcttgagtg gatgggaggg atcatcccta tctttggtac agcaaactac    180
gcacagaagt tccagggcag agtcacgatt accgcggacg aatccacgag cacagcctac    240
atggagctga gcagcctgag atctgaggac acggccgtgt attactgtgc gagaagccag    300
gtaccatcct cctactacta cggtatggac gtctggggcc aagggacaat ggtcaccgtc    360
tcctca                                                               366
```

| SEQ ID NO: 56 | moltype = DNA  length = 333 |
|---|---|
| FEATURE | Location/Qualifiers |
| source | 1..333 |
| | mol_type = other DNA |
| | organism = Homo sapiens |

SEQUENCE: 56
```
cagtctgtgc tgactcagcc gccctcagtg tctggggccc cagggcagag ggtcaccatc     60
tcctgcactg ggggcaactc caacatcggg gcaggttatc atgtacattg gtaccagcaa    120
cttccaggag cagcccccaa actcctcatc tatggtgaca ctaatcggcc ctcaggggtc    180
cctgaccgat tctctggctc tcagtctggc acctcagcct ccctggccat cactgggctc    240
caggctgacg atgaggctga ttattactgc cagtcctatg acagaagccg gggtggttgg    300
tttttcggcg agggacccca gctgaccgtc cta                                 333
```

| SEQ ID NO: 57 | moltype = DNA  length = 357 |
|---|---|
| FEATURE | Location/Qualifiers |
| source | 1..357 |
| | mol_type = other DNA |
| | organism = Homo sapiens |

SEQUENCE: 57
```
caggtgaagc tggtggagtg gtcgctgagc gtggtccagc ctgggaggtc cctgagactc     60
tcctgcgcag cctctggatt caccttcagt agctatgcta tgcactgggt ccgccaggct    120
ccaggcaagg ggctggagtg ggtggcagtt atatcatatg atggaagcaa taaatactac    180
gcagactccg tgaagggccg attcaccatc tccagagaca attccaagaa cacgctgtat    240
ctgcaaatga acagcctgag agctgaggac acggctgtgt attactgtgc gagaggtcgt    300
gaatactact actacatgga cgtctgggcc aaagggacca cggtcagcgt ctcctca       357
```

| SEQ ID NO: 58 | moltype = DNA  length = 318 |
|---|---|
| FEATURE | Location/Qualifiers |
| source | 1..318 |
| | mol_type = other DNA |
| | organism = Homo sapiens |

SEQUENCE: 58
```
cagtctgtgc tgactcagcc accctcagtg tcagtggccc caggaaagac ggccaggatt     60
acatgtgggg gatacaacat tgcaagaaaa agtgtgcact ggtaccagca gaagccaggc    120
caggcccctg tgttggtcat gtataatgat aacgaccggc cctcaggaat ccctgagcga    180
ttctctggct ccaactctgg gaacacggcc accctgacca tcagcagggt cgaagccggg    240
gatgaggccg actattactg tcaggtgtgg gataatagtg attatgtctt cggaactggg    300
accaaggtca ccgtcccta                                                 318
```

| SEQ ID NO: 59 | moltype = DNA  length = 360 |
|---|---|
| FEATURE | Location/Qualifiers |
| source | 1..360 |
| | mol_type = other DNA |
| | organism = Homo sapiens |

SEQUENCE: 59
```
caggtgcagt tgatgcagtc tggggctgag gtgaagaagc ctggggcctc agtgaaggtt     60
tcctgcaagg catctggata caccttcacc agctactgga tgcactgggt gcgacaggcc    120
cctggacaag ggcttgagtg gatgggaata atcaaccta gtggtggtag cacaagctac    180
gcacagaagt tccagggcag agtcaccatg accaggaca cgtccacgag cacagtctac    240
atggagctga gcagcctgag atctgaggac acggccgtgt attactgtgc gagaggattc    300
ggctacggt gtaaggccct tgactactgg ggccagggaa ccacggtcac cgtctcttca    360
```

| SEQ ID NO: 60 | moltype = DNA  length = 321 |
|---|---|
| FEATURE | Location/Qualifiers |
| source | 1..321 |
| | mol_type = other DNA |
| | organism = Homo sapiens |

SEQUENCE: 60
```
gacatccaga tgacccagtc tcctcccacc ctgtctgcat ctgtagggga cagagtcacc     60
atcacttgcc gggccagtca gaatattaat agtaggttgg cctggtatca gcagaaacca    120
gggagagccc ctaaactcct gatctataag gcgtctactt tagagagtgg ggtcccatcg    180
aggttcagcg gcagtggatc tgggacagaa ttcactctca ccatcagcag cctgcagcca    240
```

```
gatgactttg caacttatta ctgccaacag tttgataaat attcgatcac tttcggcgga    300
gggaccaaga tggagatcaa a                                              321
```

| SEQ ID NO: 61 | moltype = AA  length = 118 |
|---|---|
| FEATURE | Location/Qualifiers |
| source | 1..118 |
|  | mol_type = protein |
|  | organism = Homo sapiens |

SEQUENCE: 61
```
QVQLQQLGPG LVKPSETLSL TCNVSGGSVS RGSHYWTWIR QPPGKGLEWI GYIHTDGSTN    60
FNPSLKSRVT MSLDRSRNQF SLTLSSVTAT DTAVYYCARE PGGALNFWGQ GTLVTVSS    118
```

| SEQ ID NO: 62 | moltype = AA  length = 110 |
|---|---|
| FEATURE | Location/Qualifiers |
| source | 1..110 |
|  | mol_type = protein |
|  | organism = Homo sapiens |

SEQUENCE: 62
```
DFMLTQPPST SGTPGQRVTI SCSGSSSNIG SNTVNWYQQL PGTAPKLLIY SNNQRPSGVP    60
DRFSGSKSGT SASLAISGLQ SEDEADYYCA SWDDSLNGVV FGGGTTVTVL             110
```

| SEQ ID NO: 63 | moltype = AA  length = 126 |
|---|---|
| FEATURE | Location/Qualifiers |
| source | 1..126 |
|  | mol_type = protein |
|  | organism = Homo sapiens |

SEQUENCE: 63
```
QVQLVQSGAE VKKPGASVKV SCKASGYTFT GYYMHWVRQA PGQGLEWMGR INPNSGGTNY    60
AQKFQGRVTM TRDTSISTAY MELSRLRSDD TAVYYCASGK TYYDFWSGGR RGMDVWGQGT   120
MVTVSS                                                             126
```

| SEQ ID NO: 64 | moltype = AA  length = 107 |
|---|---|
| FEATURE | Location/Qualifiers |
| source | 1..107 |
|  | mol_type = protein |
|  | organism = Homo sapiens |

SEQUENCE: 64
```
DIQLTQSPSS LSASVGDRVT ITCRAGQSVS RYLNWFQQKP GKAPKLLIYT SSNLQSGVPS    60
RFSASGSGTD FTLTISSLQP EDFATYYCQQ TYSTPWTFGQ GTKLEIK                107
```

| SEQ ID NO: 65 | moltype = AA  length = 122 |
|---|---|
| FEATURE | Location/Qualifiers |
| source | 1..122 |
|  | mol_type = protein |
|  | organism = Homo sapiens |

SEQUENCE: 65
```
QVQLVQSGAE VKKPGSSVKV SCKASGGTFS SYAISWVRQA PGQGLEWMGG IIPIFGTANY    60
AQKFQGRVTI TADESTSTAY MELSSLRSED TAVYYCARSQ VPSSYYYGMD VWGQGTMVTV   120
SS                                                                 122
```

| SEQ ID NO: 66 | moltype = AA  length = 111 |
|---|---|
| FEATURE | Location/Qualifiers |
| source | 1..111 |
|  | mol_type = protein |
|  | organism = Homo sapiens |

SEQUENCE: 66
```
QSVLTQPPSV SGAPGQRVTI SCTGGNSNIG AGYHVHWYQQ LPGAAPKLLI YGDTNRPSGV    60
PDRFSGSQSG TSASLAITGL QADDEADYYC QSYDRSGGW FFGGGTQLTV L           111
```

| SEQ ID NO: 67 | moltype = AA  length = 119 |
|---|---|
| FEATURE | Location/Qualifiers |
| source | 1..119 |
|  | mol_type = protein |
|  | organism = Homo sapiens |

SEQUENCE: 67
```
QVKLVEWSLS VVQPGRSLRL SCAASGFTFS SYAMHWVRQA PGKGLEWVAV ISYDGSNKYY    60
ADSVKGRFTI SRDNSKNTLY LQMNSLRAED TAVYYCARGR EYYYYMDVWG KGTTVSVSS   119
```

| SEQ ID NO: 68 | moltype = AA  length = 106 |
|---|---|
| FEATURE | Location/Qualifiers |
| source | 1..106 |
|  | mol_type = protein |
|  | organism = Homo sapiens |

SEQUENCE: 68
```
QSVLTQPPSV SVAPGKTARI TCGGYNIARK SVHWYQQKPG QAPVLVMYND NDRPSGIPER    60
FSGSNSGNTA TLTISRVEAG DEADYYCQVW DNSDYVFGTG TKVTVL                 106
```

| SEQ ID NO: 69 | moltype = AA  length = 120 |
|---|---|
| FEATURE | Location/Qualifiers |

```
source               1..120
                     mol_type = protein
                     organism = Homo sapiens
SEQUENCE: 69
QVQLMQSGAE VKKPGASVKV SCKASGYTFT SYYMHWVRQA PGQGLEWMGI INPSGGSTSY    60
AQKFQGRVTM TRDTSTSTVY MELSSLRSED TAVYYCARGF GYGGKALDYW GQGTTVTVSS   120

SEQ ID NO: 70        moltype = AA  length = 107
FEATURE              Location/Qualifiers
source               1..107
                     mol_type = protein
                     organism = Homo sapiens
SEQUENCE: 70
DIQMTQSPPT LSASVGDRVT ITCRASQNIN SRLAWYQQKP GRAPKLLIYK ASTLESGVPS    60
RFSGSGSGTE FTLTISSLQP DDFATYYCQQ FDKYSITFGG GTKMEIK                 107
```

LEPTIN ANTIBODIES AND METHOD OF REDUCING LEPTIN

REFERENCE TO A SEQUENCE LISTING

A Sequence Listing in xml format is incorporated by reference into the specification. The name of the xml file containing the Sequence Listing is UTSD3647.xml. The file is 65,881 bytes and was created on Aug. 5, 2023 and submitted electronically via EFS-Web.

INTRODUCTION

Leptin is a hormone produced by adipocytes and is elevated in obesity. The congenital lack of leptin results in obesity and the metabolism field widely accepts the concept. Upon cloning of the leptin gene, the original hope was that leptin would act as a break for further food intake and a trigger to increase energy expenditure. The hope was that the injection of recombinant leptin would act as an effective weight loss mechanism. However, these hopes were quickly disappointed, since obese individuals have high leptin levels, but the individual is leptin resistant. Not even the injection of very high leptin levels can overcome this resistance.

We generated a battery of monoclonal antibodies against human and mouse leptin. These antibodies showed strong binding affinities to human leptin and significant neutralizing activity in vivo. More importantly, treatment of high-fat diet (HFD)-fed mice with neutralizing antibodies reduces body-weight gain and confirmed findings in mice with genetic knock-down of leptin. Our antibodies provide effective for treatment of obesity with high level of leptin but resistant to the conventional leptin treatment.

SUMMARY OF THE INVENTION

In an aspect the invention provides an antibody antigen binding domain which specifically binds human leptin, and comprises $V_H$ or $V_L$ CDR1, CDR2 and CDR3 sequences of an hLept antibody:

| VH | CDR1 | CDR2 | CDR3 |
|---|---|---|---|
| hLept-1$V_H$ | GGSVSRGSHY (SEQ ID NO: 1) | IHTDGST (SEQ ID NO: 2) | AREPGGALNF (SEQ ID NO: 3) |
| hLept-2$V_H$ | GYTFTGYY (SEQ ID NO: 4) | INPNSGGT (SEQ ID NO: 5) | ASGKTYYDFWSGGRRGMDV (SEQ ID NO: 6) |
| hLept-3$V_H$ | GGTFSSYA (SEQ ID NO: 7) | IIPIFGTA (SEQ ID NO: 8) | ARSQVPSSYYYGMDV (SEQ ID NO: 9) |
| hLept-5$V_H$ | GFTFSSYA (SEQ ID NO: 10) | ISYDGSNK (SEQ ID NO: 11) | ARGREYYYYMDV (SEQ ID NO: 12) |
| hLept-6$V_H$ | GYTFTSYY (SEQ ID NO: 13) | INPSGGST (SEQ ID NO: 14) | ARGFGYGGKALDY (SEQ ID NO: 15) |

| VL | CDR1 | CDR2 | CDR3 |
|---|---|---|---|
| hLept-1$V_L$ | SSNIGSNT (SEQ ID NO: 16) | SNN | ASWDDSLNGVV (SEQ ID NO: 17) |
| hLept-2$V_L$ | QSVSRY (SEQ ID NO: 18) | TSS | QQTYSTPWT (SEQ ID NO: 19) |
| hLept-3$V_L$ | NSNIGAGYH (SEQ ID NO: 20) | GDT | QSYDRSRGGWF (SEQ ID NO: 21) |
| hLept-5$V_L$ | NIARKS (SEQ ID NO: 22) | NDN | QVWDNSDYV (SEQ ID NO: 23) |
| hLept-6$V_L$ | QNINSR (SEQ ID NO: 24) | KAS | QQFDKYSIT (SEQ ID NO: 25) |

The $V_H$ and $V_L$ CDR1, CDR2 and CDR3 sequences of the hLept antibodies can be combined in alternative combinations which bind human leptin, i.e. the CDRs of hLept-1$V_H$ can be paired with the CDRs of hLept-1-$V_L$, hLept-2$V_L$, hLept-3$V_L$, hLept-5$V_L$ or hLept-6$V_L$.

In embodiments the antigen binding domain comprises:
$V_H$ and $V_L$ CDR1, CDR2 and CDR3 sequences of the hLept antibody;
$V_H$ or $V_L$ sequences of the hLept antibody; and/or
$V_H$ and $V_L$ sequences of the hLept antibody.

In embodiments the antigen binding domain is part of a monoclonal IgG antibody and/or a humanized antibody.

In other aspects the invention provides an expression vector encoding the antibody antigen binding domain or a cultured cell expressing the antibody antigen binding domain.

In another aspect the invention provides a method of using the antibody antigen binding domain to treat obesity or diabetes, comprising the step of administering the domain to a person in need thereof.

The invention includes all combinations of the recited particular embodiments.

BRIEF DESCRIPTION OF THE DRAWINGS

FIG. 1A. Antibody therapy reduces body weight.
FIG. 1B. Antibody therapy reduces food intake.
FIG. 1C. Antibody therapy increases leptin transcription in brown and epididymal adipose tissue.
FIG. 1D. Antibody therapy improves glucose homeostasis.
FIG. 1E. Antibody therapy reduces high fat diet effects on brown adipose tissue.

DESCRIPTION OF PARTICULAR EMBODIMENTS OF THE INVENTION

Unless the context indicates otherwise, the term "antibody" is used in the broadest sense and specifically covers antibodies (including full length monoclonal antibodies) and antibody fragments. An antibody molecule is usually monospecific, but may also be described as idiospecific, heterospecific, or polyspecific. Antibody molecules bind by means of specific binding sites to specific antigenic determinants or epitopes on antigens. "Antibody fragments" comprise a portion of a full length antibody, generally the antigen binding or variable region thereof. Examples of antibody fragments include Fab, Fab', F(ab').sub.2, and Fv fragments; diabodies; linear antibodies; single-chain antibody molecules; and multispecific antibodies formed from antibody fragments.

Natural and engineered antibody structures are well known in the art, e.g. Strohl et al., *Therapeutic antibody engineering: Current and future advances driving the strongest growth area in the pharmaceutical industry*, Woodhead Publishing Series in Biomedicine No. 11, October 2012; Holliger et al. Nature Biotechnol 23, 1126-1136 (2005); Chames et al. Br J Pharmacol. 2009 May; 157(2): 220-233.

Monoclonal antibodies (MAbs) may be obtained by methods known to those skilled in the art. See, for example Kohler et al (1975); U.S. Pat. No. 4,376,110; Ausubel et al (1987-1999); Harlow et al (1988); and Colligan et al (1993). The mAbs of the invention may be of any immunoglobulin class including IgG, IgM, IgE, IgA, and any subclass thereof. A hybridoma producing a mAb may be cultivated in vitro or in vivo. High titers of mAbs can be obtained in in vivo production where cells from the individual hybridomas are injected intraperitoneally into mice, such as pristine-primed Balb/c mice to produce ascites fluid containing high concentrations of the desired mAbs. MAbs of isotype IgM or IgG may be purified from such ascites fluids, or from culture supernatants, using column chromatography methods well known to those of skill in the art.

An "isolated polynucleotide" refers to a polynucleotide segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA, which is part of a hybrid gene encoding additional polypeptide sequence.

A "construct" means any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more polynucleotide molecule has been linked in a functionally operative manner, i.e. operably linked. A recombinant construct will typically comprise the polynucleotides of the invention operably linked to transcriptional initiation regulatory sequences that will direct the transcription of the polynucleotide in the intended host cell. Both heterologous and non-heterologous (i.e., endogenous) promoters can be employed to direct expression of the nucleic acids of the invention.

A "vector" refers any recombinant polynucleotide construct that may be used for the purpose of transformation, i.e. the introduction of heterologous DNA into a host cell. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors".

An "expression vector" as used herein refers to a nucleic acid molecule capable of replication and expressing a gene of interest when transformed, transfected or transduced into a host cell. The expression vectors comprise one or more phenotypic selectable markers and an origin of replication to ensure maintenance of the vector and to, if desired, provide amplification within the host. The expression vector further comprises a promoter to drive the expression of the polypeptide within the cells. Suitable expression vectors may be plasmids derived, for example, from pBR322 or various pUC plasmids, which are commercially available. Other expression vectors may be derived from bacteriophage, phagemid, or cosmid expression vectors.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

EXAMPLES

Panning and Selection Of Anti-Leptin Monoclonal Antibodies Using In-House Prepared scFv Phage Display Human Antibody Library Leptin protein (NM-000230, Entrez 3952: Sino Biologics) was used to panning the phage display scFv library (diversity of $1 \times 10^{11}$). Binders were selected by phage ELISA by coating LEPTIN protein on 96-well plates (max-sorb plates, Nunc) and were detected with an anti-M13 phage antibody conjugated with horseradish peroxidase (HRP) and TMB substrate (cell signaling). DNA sequences contained in phage-mid vector is isolated using a plasmid preparation kit and sequenced (Genewiz). Complete heavy chain variable region and light chain variable sequences were amplified and expressed into full IgG using an expression vector system in HEK293 cells.

Selected LEPTIN binding hits were expressed as human IgGs using a mammalian expression vector system in human embryonic kidney (HEK293) cells (Invitrogen). Antibodies were purified using a column with protein A resin by a fast protein liquid chromatography (FPLC) separation unit. Purified LEPTIN binding antibodies were characterized for their biological properties.

Binding Affinity of Anti-Leptin Monoclonal Antibodies

Binding of LEPTIN by monoclonal antibodies was first screened by ELISA using supernatants collected from the B cell cultures. Human or mouse LEPTIN protein (Sino Biologicals) was coated on a 96-well high binding plate over night at 4° C. in PBS. B cell culture supernatants (5 µl medium and 95 µl of PBS) were added at for binding to LEPTIN antigen coated on the plate. Bound antibody was detected using a secondary antibody against rabbit IgG conjugated with HRP and TMB substrate.

Binding to human leptin in ELISA (1:20 diluted culture supernatants; signals: absorbance at 450 nM):

| hLept-1/ | hLept-2/ | hLept-3/ | hLept-5/ | hLept-6/ |
|---|---|---|---|---|
| 0.071 | 2.5739 | 0.1902 | 0.7385 | 0.663 |

ELISA titration was used to determine the binding affinity of a panel of monoclonal antibodies to LEPTIN antigen. Binding constants ($K_D$ and/or EC 50) of a panel of monoclonal antibodies were estimated using the 4 parameter curve fitting with Prism GraphPad program. For Biacore analysis, all experiments were performed at 25° C. at a flow rate of 45 µl/min. An anti-human IgG Fc antibody (from ThermoFisher, at 50 µg/ml each in acetate buffer, pH 5.0) was immobilized onto a carboxymethyl dextran sensorchip (CMS) using amine coupling procedures based on instruction from the manufacturer. Purified rabbit/human chimeric antibody to be tested was diluted at a concentration of 5 µg/ml in 0.5% P20, HBS-EP buffer and injected on FC2 to reach 500 to 1000 RU. FC1 was used as the reference cell. Specific signals correspond to the difference of signals obtained on FC2 versus FC1. The analyte (recombinant human LEPTIN, apparent molecular weight 16 kDa on SDS-PAGE gel) was injected during 90 sec at series of concentration dilutions (100, 50, 25, 12.5, 6.25, and 3.13, 1.56 nM) in 0.5% P20, HBS-EP buffer. These concentrations were prepared from stock solution in 0.5% P20, HBS-EP. The dissociation phase of the analyte was monitored over a 30 minutes period. Running buffer was also injected under the same conditions as a double reference. After each running cycle, both flow cells were regenerated by injecting 20 to 45 µl of Glycine-HCl buffer pH 1.5. Binding $K_D$ on LEPTIN was calculated by $k_{off}/k_{on}$ kinetic rate for each LEPTIN monoclonal antibodies (Table 3).

Neutralizing Leptin Antibodies Confer Reduced Weight Gain

We used a cohort of mice that had previously been exposed to 10 weeks of high fat diet exposure. We treated these mice twice a week either with PBS, low ("0.5 microgram/g BW), medium (5 microgram/g BW) or high (50 microgram/g BW) leptin antibody injections for up to 20 days; hLept-1, hLept-2, hLetp-3, hLept-5 and hLept-6 antibody injections provide consistent dose dependent results. As seen in FIG. 1A, there is a dose-dependent effect of these injections in terms of impaired weight gain. While all animals initially lost some weight, control mice and lower doses of antibody had some effect, whereas with the highest dose of antibody, overall weight reduction persisted. There was a dose-dependent reduction in food intake (FIG. 1B), as well as a dose-dependent transcriptional increase for leptin in brown and epididymal adipose tissue, with more limited compensatory effects in subcutaneous adipose tissue (FIG. 1C). Antibody treatment leads to an effective 40% reduction of circulating leptin levels, sufficient to achieve a significant degree of leptin sensitization. Leptin-neutralization not only effectively reduces the weight, but with the weight reduction we also see the expected improvements in glucose homeostasis (FIG. 1D). Furthermore, high fat diet generally affects brown adipose tissue negatively and lead to an increased "whitening" of BAT, and this process is significantly prevented and/or reversed by our antibody treatment (FIG. 1E). Concomitantly, we also observed a reduction in hepatic steatosis.

TABLE 1

| CDR* sequences of heavy chain variable sequences of leptin antibodies | | | |
|---|---|---|---|
| Name | CDR1 | CDR2 | CDR3 |
| hLept-1 | Ggtggctccgtcagcaga ggtagtcactac (SEQ ID NO: 26) GGSVSRGSHY (SEQ ID NO: 1) | Atccacaccgatgggagc acc (SEQ ID NO: 27) IHTDGST (SEQ ID NO: 2) | Gcgagagagcccgggggcgccct gaatttc (SEQ ID NO: 28) AREPGGALNF (SEQ ID NO: 3) |

TABLE 1-continued

CDR* sequences of heavy chain variable sequences of leptin antibodies

| Name | CDR1 | CDR2 | CDR3 |
|---|---|---|---|
| hLept-2 | Ggatacaccttcaccggctactat (SEQ ID NO: 29) GYTFTGYY (SEQ ID NO: 4) | Atcaaccctaacagtggtgcaca (SEQ ID NO: 30) INPNSGGT (SEQ ID NO: 5) | Gcgagtgggaaaacgtattacgattttggagtggtgggagacgcggtatggacgtc (SEQ ID NO: 31) ASGKTYYDFWSGGRRGMDV (SEQ ID NO: 6) |
| hLept-3 | Ggaggcaccttcagcagctatgct (SEQ ID NO: 32) GGTFSSYA (SEQ ID NO: 7) | Atcatccctatctttggtacagca (SEQ ID NO: 33) IIPIFGTA (SEQ ID NO: 8) | Gcgagaagccaggtaccatcctcctactactacggtatggacgtc (SEQ ID NO: 34) ARSQVPSSYYYGMDV (SEQ ID NO: 9) |
| hLept-5 | Ggattcaccttcagtagctatgct (SEQ ID NO: 35) GFTFSSYA (SEQ ID NO: 10) | Atatcatatgatggaagcaataaa (SEQ ID NO: 36) ISYDGSNK (SEQ ID NO: 11) | Gcgagaggtcgtgaatactactactacatggacgtc (SEQ ID NO: 37) ARGREYYYYMDV (SEQ ID NO: 12) |
| hLept-6 | Ggatacaccttcaccagctactat (SEQ ID NO: 38) GYTFTSYY (SEQ ID NO: 13) | Atcaaccctagtggtggtgcaca (SEQ ID NO: 39) INPSGGST (SEQ ID NO: 14) | Gcgagaggattcggctacggtggtaaggcccttgactac (SEQ ID NO: 40) ARGFGYGGKALDY (SEQ ID NO: 15) |

*CDRs are defined based on online antibody sequence analytical tool (IMGT).

TABLE 2

List of CDR sequences for light chain of each antibodies

| Name | CDR1 | CDR2 | CDR3 |
|---|---|---|---|
| hLept-1 | Agctccaacatcggaagtaatact (SEQ ID NO: 41) SSNIGSNT (SEQ ID NO: 16) | agtaataat SNN | Gcatcatgggatgacagcctgaatggtgtggta (SEQ ID NO: 42) ASWDDSLNGVV (SEQ ID NO: 17) |
| hLept-2 | Cagagcgttagcaggtat (SEQ ID NO: 43) QSVSRY (SEQ ID NO: 18) | acttcatcc TSS | Caacagacttacagtaccccgtggacg (SEQ ID NO: 44) QQTYSTPWT (SEQ ID NO: 19) |
| hLept-3 | Aactccaacatcggggcattatcat (SEQ ID NO: 45) NSNIGAGYH (SEQ ID NO: 20) | ggggtgacact GDT | Cagtcctatgacagaagccggggtggttggttt (SEQ ID NO: 46) QSYDRSRGGWF (SEQ ID NO: 21) |
| hLept-5 | Aacattgcaagaaaaagt (SEQ ID NO: 47) NIARKS (SEQ ID NO: 22) | aatgataac NDN | caggtgtgggataatagtgattatgtc (SEQ ID NO: 48) QVWDNSDYV (SEQ ID NO: 23) |
| hLept-6 | Cagaatattaatagtagg (SEQ ID NO: 49) QNINSR (SEQ ID NO: 24) | aaggcgtct KAS | Caacagtttgataaatattcgatcact (SEQ ID NO: 50) QQFDKYSIT (SEQ ID NO: 25) |

TABLE 3

Binding affinities of anti-Leptin antibodies determined by ELISA

| Antibody name | EC50 |
|---|---|
| hLept-1 | 1-500 nM |
| hLept-2 | 1-500 nM |
| hLept-3 | 1-500 nM |
| hLept-5 | 1-500 nM |
| hLept-6 | 1-500 nM |

Appendix I. Variable DNA sequences of anti-leptin antibodies

>hLept1_HCv
(SEQ ID NO: 51)
CAGGTACAGCTGCAGCAGTTGGGCCCAGGACTGGTGAAGCCTTCGGAGACCCTGTCCCTCACCT

GCAATGTCTCTGGTGGCTCCGTCAGCAGAGGTAGTCACTACTGGACCTGGATCCGGCAGCCCCC

AGGAAAGGGACTGGAGTGGATTGGGTATATCCACACCGATGGGAGCACCAACTTCAATCCCTCC

CTCAAGAGTCGAGTCACCATGTCACTAGACAGGTCCAGGAACCAGTTCTCCCTGACGCTGAGCT

CTGTGACCGCTACGGACACGGCCGTTTATTATTGTGCGAGAGAGCCCGGGGGCGCCCTGAATTT

CTGGGGCCAGGGAACCCTGGTCACCGTCTCCTCA

>hLept1_LCv
(SEQ ID NO: 52)
AATTTTATGCTGACTCAGCCACCCTCAACGTCTGGGACCCCCGGGCAGAGGGTCACCATCTCTT

GTTCTGGAAGCAGCTCCAACATCGGAAGTAATACTGTAAACTGGTACCAGCAGCTCCCAGGAAC

GGCCCCCAAACTCCTCATCTATAGTAATAATCAGCGGCCCTCAGGGGTCCCTGACCGATTCTCT

GGCTCCAAGTCTGGCACCTCAGCCTCCCTGGCCATCAGTGGGCTCCAGTCTGAGGATGAGGCTG

ATTATTATTGTGCATCATGGGATGACAGCCTGAATGGTGTGGTATTCGGCGGAGGGACCACGGT

GACCGTCCTG

>hLept2_HCv
(SEQ ID NO: 53)
CAGGTGCAGCTGGTGCAGTCTGGGGCTGAGGTGAAGAAGCCTGGGGCCTCAGTGAAGGTCTCCT

GCAAGGCTTCTGGATACACCTTCACCGGCTACTATATGCACTGGGTGCGACAGGCCCCTGGACA

AGGGCTTGAGTGGATGGGACGGATCAACCCTAACAGTGGTGGCACAAACTATGCACAGAAGTTT

CAGGGCAGGGTCACCATGACCAGGGACACGTCCATCAGCACAGCCTACATGGAGCTGAGCAGGC

TGAGATCTGACGACACGGCCGTGTATTACTGTGCGAGTGGGAAAACGTATTACGATTTTTGGAG

TGGTGGGAGACGCGGTATGGACGTCTGGGGCCAAGGGACAATGGTCACCGTCTCTTCA

>hLept2_LCv
(SEQ ID NO: 54)
GACATCCAGTTGACCCAGTCTCCATCCTCCCTGTCTGCATCTGTAGGAGACAGAGTCACCATCA

CTTGCCGGGCAGGTCAGAGCGTTAGCAGGTATTTAAATTGGTTTCAGCAGAAACCAGGGAAAGC

CCCTAAGCTCCTCATCTATACTTCATCCAATTTGCAAAGTGGGGTCCCATCAAGGTTCAGTGCC

AGTGGATCTGGGACAGATTTCACTCTCACCATCAGCAGTCTGCAACCTGAGGATTTTGCTACCT

ACTACTGTCAACAGACTTACAGTACCCCGTGGACGTTCGGCCAAGGGACCAAGCTGGAGATCAA

A

>hLept3_HCv
(SEQ ID NO: 55)
CAGGTGCAGCTGGTGCAGTCTGGGGCTGAGGTGAAGAAGCCTGGGTCCTCGGTGAAGGTCTCCT

GCAAGGCTTCTGGAGGCACCTTCAGCAGCTATGCTATCAGCTGGGTGCGACAGGCCCCTGGACA

AGGGCTTGAGTGGATGGGAGGGATCATCCCTATCTTTGGTACAGCAAACTACGCACAGAAGTTC

CAGGGCAGAGTCACGATTACCGCGGACGAATCCACGAGCACAGCCTACATGGAGCTGAGCAGCC

TGAGATCTGAGGACACGGCCGTGTATTACTGTGCGAGAAGCCAGGTACCATCCTCCTACTACTA

CGGTATGGACGTCTGGGGCCAAGGGACAATGGTCACCGTCTCCTCA

>hLept 3_LCv
(SEQ ID NO: 56)
CAGTCTGTGCTGACTCAGCCGCCCTCAGTGTCTGGGGCCCCAGGGCAGAGGGTCACCATCTCCT

GCACTGGGGGCAACTCCAACATCGGGGCAGGTTATCATGTACATTGGTACCAGCAACTTCCAGG

-continued

AGCAGCCCCCAAACTCCTCATCTATGGTGACACTAATCGGCCCTCAGGGGTCCCTGACCGATTC

TCTGGCTCTCAGTCTGGCACCTCAGCCTCCCTGGCCATCACTGGGCTCCAGGCTGACGATGAGG

CTGATTATTACTGCCAGTCCTATGACAGAAGCCGGGGTGGTTGGTTTTTCGGCGGAGGGACCCA

GCTGACCGTCCTA

>hLept5_HCv (SEQ ID NO: 57)
CAGGTGAAGCTGGTGGAGTGGTCGCTGAGCGTGGTCCAGCCTGGGAGGTCCCTGAGACTCTCCT

GCGCAGCCTCTGGATTCACCTTCAGTAGCTATGCTATGCACTGGGTCCGCCAGGCTCCAGGCAA

GGGGCTGGAGTGGGTGGCAGTTATATCATATGATGGAAGCAATAAATACTACGCAGACTCCGTG

AAGGGCCGATTCACCATCTCCAGAGACAATTCCAAGAACACGCTGTATCTGCAAATGAACAGCC

TGAGAGCTGAGGACACGGCTGTGTATTACTGTGCGAGAGGTCGTGAATACTACTACTACATGGA

CGTCTGGGGCAAAGGGACCACGGTCAGCGTCTCCTCA

>hLept5_LCv (SEQ ID NO: 58)
CAGTCTGTGCTGACTCAGCCACCCTCAGTGTCAGTGGCCCCAGGAAAGACGGCCAGGATTACAT

GTGGGGATACAACATTGCAAGAAAAAGTGTGCACTGGTACCAGCAGAAGCCAGGCCAGGCCCC

TGTGTTGGTCATGTATAATGATAACGACCGGCCCTCAGGGATCCCTGAGCGATTCTCTGGCTCC

AACTCTGGGAACACGGCCACCCTGACCATCAGCAGGGTCGAAGCCGGGGATGAGGCCGACTATT

ACTGTCAGGTGTGGGATAATAGTGATTATGTCTTCGGAACTGGGACCAAGGTCACCGTCCTA

>hLept6_HCv (SEQ ID NO: 59)
CAGGTGCAGTTGATGCAGTCTGGGGCTGAGGTGAAGAAGCCTGGGGCCTCAGTGAAGGTTTCCT

GCAAGGCATCTGGATACACCTTCACCAGCTACTATATGCACTGGGTGCGACAGGCCCCTGGACA

AGGGCTTGAGTGGATGGGAATAATCAACCCTAGTGGTGGTAGCACAAGCTACGCACAGAAGTTC

CAGGGCAGAGTCACCATGACCAGGGACACGTCCACGAGCACAGTCTACATGGAGCTGAGCAGCC

TGAGATCTGAGGACACGGCCGTGTATTACTGTGCGAGAGGATTCGGCTACGGTGGTAAGGCCCT

TGACTACTGGGGCCAGGGAACCACGGTCACCGTCTCTTCA

>hLept6_LCv (SEQ ID NO: 60)
GACATCCAGATGACCCAGTCTCCTCCCACCCTGTCTGCATCTGTAGGGGACAGAGTCACCATCA

CTTGCCGGGCCAGTCAGAATATTAATAGTAGGTTGGCCTGGTATCAGCAGAAACCAGGGAGAGC

CCCTAAACTCCTGATCTATAAGGCGTCTACTTTAGAGAGTGGGGTCCCATCGAGGTTCAGCGGC

AGTGGATCTGGGACAGAATTCACTCTCACCATCAGCAGCCTGCAGCCAGATGACTTTGCAACTT

ATTACTGCCAACAGTTTGATAAATATTCGATCACTTTCGGCGGAGGGACCAAGATGGAGATCAA

A

Appendix II. Variable amino acid sequences of anti-leptin antibodies

>hLept1_HCv_AA (SEQ ID NO: 61)
QVQLQQLGPGLVKPSETLSLTCNVSGGSVSRGSHYWTWIRQPPGKGLEW
IGYIHTDGSTNFNPSLKSRVTMSLDRSRNQFSLTLSSVTATDTAVYYCA
REPGGALNEWGQGTLVTVSS >hLept1_LCv_AA (SEQ ID NO: 62)
DFMLTQPPSTSGTPGQRVTISCSGSSSNIGSNTVNWYQQLPGTAPKLLI
YSNNQRPSGVPDRFSGSKSGTSASLAISGLQSEDEADYYCASWDDSLNG
VVFGGGTTVTVL >hLept2_HCv_AA (SEQ ID NO: 63)
QVQLVQSGAEVKKPGASVKVSCKASGYTFTGYYMHWVRQAPGQGLEWMG
RINPNSGGTNYAQKFQGRVTMTRDTSISTAYMELSRLRSDDTAVYYCAS
GKTYYDFWSGGRRGMDVWGQGTMVTVSS >hLept2_LCv_AA (SEQ ID NO: 64)
DIQLTQSPSSLSASVGDRVTITCRAGQSVSRYLNWFQQKPGKAPKLLIY
TSSNLQSGVPSRFSASGSGTDFTLTISSLQPEDFATYYCQQTYSTPWTF
GQGTKLEIK -continued >hLept3_HCv_AA
(SEQ ID NO: 65)
QVQLVQSGAEVKKPGSSVKVSCKASGGTFSSYAISWVRQAPGQGLEWMG
GIIPIFGTANYAQKFQGRVTITADESTSTAYMELSSLRSEDTAVYYCAR
SQVPSSYYYGMDVWGQGTMVTVSS >hLept3_HCv_AA
(SEQ ID NO: 66)
QSVLTQPPSVSGAPGQRVTISCTGGNSNIGAGYHVHWYQQLPGAAPKLL
IYGDTNRPSGVPDRFSGSQSGTSASLAITGLQADDEADYYCQSYDRSRG
GWFFGGGTQLTVL >hLept5_HCv_AA
(SEQ ID NO: 67)
QVKLVEWSLSVVQPGRSLRLSCAASGFTFSSYAMHWVRQAPGKGLEWVA
VISYDGSNKYYADSVKGRFTISRDNSKNTLYLQMNSLRAEDTAVYYCAR
GREYYYYMDVWGKGTTVSVSS >hLept5_LCv_AA
(SEQ ID NO: 68)
QSVLTQPPSVSVAPGKTARITCGGYNIARKSVHWYQQKPGQAPVLVMYN
DNDRPSGIPERFSGSNSGNTATLTISRVEAGDEADYYCQVWDNSDYVFG
TGTKVTVL >hLept6_HCv_AA
(SEQ ID NO: 69)
QVQLMQSGAEVKKPGASVKVSCKASGYTFTSYYMHWVRQAPGQGLEWMG
IINPSGGSTSYAQKFQGRVTMTRDTSTSTVYMELSSLRSEDTAVYYCAR
GFGYGGKALDYWGQGTTVTVSS >hLept6_LCv_AA
(SEQ ID NO: 70)
DIQMTQSPPTLSASVGDRVTITCRASQNINSRLAWYQQKPGRAPKLLIY
KASTLESGVPSRFSGSGSGTEFTLTISSLQPDDFATYYCQQFDKYSITF
GGGTKMEIK

What is claimed is:

1. An isolated antibody designated hLept3 that binds human leptin and comprises $V_H$ CDR1, CDR2 and CDR3 sequences: GGTFSSYA (SEQ ID NO:7), IIPIFGTA (SEQ ID NO:8), and ARSQVPSSYYYGMDV (SEQ ID NO:9), and $V_L$ CDR1, CDR2 and CDR3 sequences: NSNIGAGYH (SEQ ID NO:20), GDT, and QSYDRSRGGWF (SEQ ID NO:21).

2. The antibody of claim 1, comprising the $V_H$ and $V_L$ sequences:

```
                                                    (SEQ ID NO: 65)
QVQLVQSGAEVKKPGSSVKVSCKASGGTFSSYAISWVRQAPGQGLEWMG
GIIPIFGTANYAQKFQGRVTITADESTSTAYMELSSLRSEDTAVYYCAR
SQVPSSYYYGMDVWGQGTMVTVSS,
and
```

```
                                                    (SEQ ID NO: 66)
QSVLTQPPSVSGAPGQRVTISCTGGNSNIGAGYHVHWYQQLPGAAPKLL
IYGDTNRPSGVPDRFSGSQSGTSASLAITGLQADDEADYYCQSYDRSRG
GWFFGGGTQLTVL
```

3. The antibody of claim 1, that is a humanized monoclonal IgG antibody.

4. A method of reducing leptin levels in a human subject, comprising administering an effective amount of the antibody of claim 1 to said subject.

* * * * *